United States Patent [19]

Khouw et al.

[11] 3,984,539

[45] Oct. 5, 1976

[54] BOVINE IMMUNOGLOBULIN ISOLATION PROCESS

[76] Inventors: Boen Tie Khouw, 52 Laurel Ave.; Michael Charles Attwell, 43 Demaris Ave., both of Toronto, Ontario, Canada

[22] Filed: Dec. 2, 1974

[21] Appl. No.: 528,796

[30] Foreign Application Priority Data

Dec. 13, 1973 Canada.............................. 188161

[52] U.S. Cl. .............................. 424/87; 260/112 B; 424/85
[51] Int. Cl.$^2$ ..................... A61K 39/40; C07G 7/00
[58] Field of Search.............. 260/112 B; 424/85, 87

[56] References Cited
UNITED STATES PATENTS

| | | | |
|---|---|---|---|
| 2,520,076 | 8/1950 | Williams et al. | 260/112 B |
| 2,543,215 | 2/1951 | Williams et al. | 260/112 B |
| 3,597,409 | 8/1971 | Breuer | 260/112 B |

*Primary Examiner*—Sam Rosen

[57] ABSTRACT

A bovine immunoglobulin fraction for administration to calves to combat scours is prepared from bovine plasma or clear bovine serum by a process of salt fractionation of crude immunoglobulins and redissolving them in aqueous solution, heating the solution to 50°–60°C, cooling and removing coagulated proteins, precipitating out the immunoglobulins by salt fractionation, separating and redissolving the precipitate in aqueous solution, purifying the solution by subjection to a molecular sieve procedure, and sterile filtering.

16 Claims, No Drawings

BOVINE IMMUNOGLOBULIN ISOLATION PROCESS

This invention relates to a bovine immunoglobulin fraction, and a method for its isolation. It also relates to a bovine immunoglobulin fraction preparation suitable for administration to new-born calves, to help prevent or help cure calf scours.

One of the major natural defense mechanisms against pathogenic organisms consists of the presence of antibodies in the tissues and fluids of animals. These antibodies are proteins, sometimes referred to as immunoglobulins, which react specifically with antigens such as pathogenic organisms and their metabolic products. The new-born calf is completely devoid of antibodies but receives its protection by ingesting colostrum, normally from the mother, which contains appreciable quantities of antibodies. For only about the first 24 hours of its life the calf is able to absorb colostral antibodies through its intestine and these colostral antibodies represent the calf's protection against disease until it develops its own antibody generating system, normally after the calf is about three weeks old.

In normal farm practice it occurs frequently that a new-born calf does not receive any or sufficient immunoglobulins from colostrum. As a result of this, a considerable proportion of young calves develop colibacillosis and "scours." The disease is characterized by severe diarrhea, dehydration and frequently results in death, and is believed to be caused by infection with coliform bacteria. Whilst the incidence and severity of this disease depend upon a number of factors (locality, climate, breed, farm condition, etc.), it is well established that colibacillosis is a serious widespread problem.

One proposal for preventing or reducing the incidence of colibacillosis and scours involves injecting a bovine immunoglobulin fraction into calves during the first few days of their lives. It has also been suggested that an injection of bovine immunoglobulin fraction into calves, which have already contracted colibacillosis, may be of considerable aid to cure the disease in conjunction with other treatments such as providing sufficient liquids and salts, antibiotics, etc. Several publications have shown a relationship between the incidence of scours and the amount of immunoglobulins in the calf's serum.

There have been attempts in the past to prepare a bovine immunoglobulin fraction which can be injected into calves to combat the disease, but problems have been encountered in preparing such a fraction which retains its activity against bacteria. The most suitable raw material for the preparation of such an immunoglobulin fraction is pooled blood from a large number of healthy, adult cattle. Large pools of blood can be collected readily and under hygienic conditions in Government-inspected abattoirs.

To obtain the suitable immunoglobulins from pooled cattle blood, the blood must be fractionated to remove, or drastically reduce the concentration of certain undesirable constituents such as blood cells, fibrinogen, albumin and enzymes, and concentrate the desired immunoglobulins. It is also necessary to eliminate agents that cause irritation, fever, and infection of all types, in the preparation of the immunoglobulin fraction, so as to yield an injectable solution with potent antibody activity but one which is also sterile, free of viruses, non-pyrogenic and non-irritating.

Past difficulties in separating immunoglobulins in reasonable yield from the other, undesirable constituents of cattle blood were due to the fact that chemical and physical procedures designed to eliminate the undesirable constituents also tended to deactivate or affect adversely the immunoglobulins. For example, 6,9-diamino-2-ethoxy- acridine lactate (Rivanol) has been widely used for the separation of globulin fractions from animal serum. However, such globulin fractions, derived from bovine serum by the use of this reagent, have been found not to contain appreciable antibody titres against coliform strains.

The desired immunoglobulins are proteins of high molecular weight, and their chemical structure and molecular shape must remain intact in order to preserve their antibody activity. Furthermore, these immunoglobulins are a heterogeneous group of proteins, varying in chemical structure and composition, molecular weight, carbohydrate content, etc. It is essential that the immunoglobulins be present and preserved in their native state in order to have a preparation which is most effective in the treatment of calf scours. Many of the constituents of cattle blood which need to be removed in order to obtain a concentrated, non-irritating, non-coagulating, non-pyrogenic, sterile and virus-free preparation of immunoglobulins, are also proteins. This is true of albumin, fibrinogen, hemoglobin and enzymes.

It is an object of the present invention to prepare an immunoglobulin fraction containing antibody activity against a wide spectrum of E. coli and other pathogenic organisms.

It is a further object of the present invention to prepare an immunoglobulin fraction containing antibody activity, in aqueous solution, for subcutaneous, intramuscular or intraperitoneal injection into young calves.

The present invention provides a simple and economical process for preparing a bovine immunoglobulin fraction. The invented process provides an injectable bovine immunoglobulin solution which meets all of the usual requirements for such veterinary preparations. It has been shown to contain appreciable quantities of antibodies against the following $E.$ $coli$ serotypes: $O_{26}K_{60}$, $O_{78}K_{80}$, $O_{101}K$ (RVC 118), $O_{115}K$ (PS 3061).

According to the present invention, therefore, there is provided a process for preparing a bovine immunoglobulin fraction active against coliform bacteria infection in young calves, which comprises the steps of precipitating out by salt fractionation crude immunoglobulins from bovine plasma or clear bovine serum, and removing the crude immunoglobulins so formed; forming an aqueous solution of the crude immunoglobulins, heating the solution to a temperature of from about 50° C to about 60° C and cooling the solution and then removing coagulated proteins; precipitating out the immunoglobulins by salt fractionation; separating and re-dissolving the precipitate in aqueous solution, purifying the solution by subjection to a molecular sieve procedure and sterile filtering.

In the above process, the technique of salt fractionation is known, as a general method of separation and isolation of proteins. It is known that globulins are generally insoluble in pure water, soluble in water containing a small amount of dissolved salts, but insoluble in water containing large amounts of dissolved salts. Thus, precipitation of such proteins from an aqueous medium can be achieved by adding a water soluble salt to the medium. The salt concentration at which precipitation of such a protein occurs varies according to which salt is being used.

Salts normally used for salt fractionation of proteins are those which are readily available and highly soluble in water. Preferred is ammonium sulfate. Others commonly used include sodium sulfate and sodium chloride. The process of the invention will therefore be described with reference to use of ammonium sulfate in salt fractionation, but without limitation thereto.

In the preferred process of the invention, clear bovine blood serum is used as the starting material. This may be obtained from blood collected as a pool from a large number of healthy animals. The blood is suitably mixed with an anti-coagulant solution, e.g. sodium citrate solution, sodium oxalate solution or sodium phosphate solution. After thorough mixing, the blood is centrifuged to separate cellular materials from the plasma, which is the source of the desired bovine immunoglobulins.

Then the plasma so obtained is treated to obtain the clear bovine serum for use in the preferred process of the invention. Such treatment involves defibrination, which is suitably accomplished by adding to the plasma a suitable calcium salt, such as calcium chloride. The amount of calcium chloride added is normally enough to give a final calcium concentration in the plasma of about 0.2% (w/v). On standing at about 20°–30° C for a period of time (e.g. about 2 hours) clot formation occurs as the fibrinogen is converted to fibrin, and the fibrin-clot is removed to give a clear bovine serum, for use in the preferred process of the invention.

As an alternative, however, bovine blood plasma may be used as the starting material in the process of the invention. In such case, the treatment of the plasma to remove fibrinogen is omitted. The cake of precipitated crude immunoglobulins, obtained after ammonium sulfate addition and filtration, in this case still contains fibrinogen. When it is subsequently dissolved in water and heated, the fibrinogen is denatured and coagulated, and is largely removed in the subsequent filtration, along with the other coagulated proteins. This alternative is less preferred, however, because it renders the filtration process more difficult, and does not result in complete removal of the fibrinogen.

In the first salt fractionation step of the process, it is preferred to add solid ammonium sulfate to the serum or plasma under continuous stirring. The solid ammonium sulfate is preferably added slowly, suitably until about half saturation with the salt is achieved. This is equivalent to about 312 gms. ammonium sulfate per liter of serum or plasma. If too much ammonium sulfate is used, above about 0.7 saturation, precipitation of albumin may occur, which is undesirable.

It is preferred to add a filter aid, such as Celite to the stirred serum/ammonium sulfate slurry prior to filtration to obtain the cake of precipitated crude immunoglobulins.

Next, an aqueous solution of the crude immunoglobulins is formed. It is necessary to have a dilute salt solution to obtain a proper solution of the immunoglobulins. Thus, it is preferred to use sodium chloride although other salts can be used if desired. Suitably, an up to about 20% (w/v) solution, preferably an 8–12% (w/v) solution, and most preferably an approximately 10% (w/v) solution of sodium chloride in water is used and the cake is dissolved in it in the amount of about 100 gms. cake per liter. Next, the solution is heated suitably to about 50°–60° C, for about 10–30 minutes, and then cooled to room temperature.

This step of heating the solution of crude immunoglobulins in solution, preferably in saline solution, is believed to have a number of important effects. It denatures and coagulates some extraneous proteins without affecting the immunoglobulins. This includes the fibrin forming proteins which may have escaped the clot formation process in the preparation of the clear bovine serum for the preferred process of the invention, or which are present as an original component of the bovine blood plasma in the process of the invention starting with the plasma. In addition, the heating step tends to inactivate enzymes which are present. Residual, active, lytic enzymes in the final immunoglobulin fraction, even in minute amounts would cause slow degradation of the immunoglobulins on storage of the final product. Further, the heating step tends to inactivate any viruses that may be present, so as to assist in rendering the final product free of pathogenic organisms which might otherwise cause spreading of disease among calves to be treated.

The heating step is best carried out in 10% aqueous sodium chloride solution at about 56° C for 15 minutes. If the temperature is too low (below about 50° C), the fibrinogen is not fully precipitated. The use of sodium chloride solution of about 10 percent concentration enables best filtration rates to be obtained in subsequent steps.

The solution is then cooled to room temperature or slightly above, and the precipitated proteins are removed by filtration or centrifugation or similar means.

The immunoglobulins are next precipitated from the filtrate. This is done by salt fractionation, preferably again by adding solid ammonium sulfate to the solution. The amount of ammonium sulfate is suitably a 0.2–0.6, preferably about a 0.4, saturation of the solution, which corresponds to about 240 gms. per liter of solution. The precipitate containing the immunoglobulins is then collected by filtration or centrifugation. The precipitate may be spun on a centrifuge so as to remove excess moisture.

So as to purify the immunoglobulin fraction so obtained, it is next dissolved in an aqueous medium, preferably saline, and subjected to a molecular sieve procedure. This is in order to remove the residual ammonium sulfate solution and put it into a form ready for injection. Suitable molecular sieve procedures include dialysis, gel filtration and reverse osmosis. Preferred is dialysis against physiological saline. Thus the precipitate obtained above is dissolved in an approximately equal weight of a 0.9% (w/v) sodium chloride aqueous solution. The solution so formed is dialyzed in a suitable apparatus against 0.9% saline solution. Suitably the dialysis may be carried out over a period of several days, and the saline solution is changed frequently during the course of dialysis. Subsequently, the dialyzed solution is clarified and sterile filtered. For economic reasons, it is preferred that the dialyzed solution be sterile filtered at a relatively fast rate, without clogging the filter medium (normally a 0.45 micron Millipore filter disc). It is therefore best to clarify the solution prior to filtration. This can in most cases be accomplished by adding filter aids such as proprietary types of diatomaceous earths marketed for such purposes, or by filtration first through an asbestos pad, by centrifugation or by ethanol fractionation and removal of the precipitate so formed. Some improvements in clarity can also be obtained by sonication of the solution, or by dilution and reconcentration. The use of filter aids of the diatomaceous earth type is preferred. The protein content of the clear solution is then adjusted to about 10—11 percent.

To prepare the solution of immunoglobulins for storage and use on calves, it is preferred to add small amounts of a protein solution stabilizer, e.g. glycine, and one or more antibacterial and preserving agents, e.g. phenol or thimerosal. A suitable amount of glycine is about 22.5 gms per liter of solution. A suitable amount of thimerosal is 0.1 gms per liter of solution. Finally, the solution may be sterile filtered through a Milli pore membrane and dispensed aseptically into appropriate sterile containers. This sterile solution of bovine immunoglobulins is then ready for injection into calves.

Instead of an injectable solution, an immunoglobulin powder can be prepared by a process according to the invention. Thus, the saline solution of immunoglobulins obtained from the dialysis step may be clarified by filtration as described, and then freeze dried to give a powder containing about 8–10% sodium chloride. This powder can then be reconstituted into a solution when required, ready for injection. Alternatively, the solution of immunoglobulins can be dialyzed against water and the resulting suspension freeze dried to give an essentially salt free powder.

The invention is further described in the following illustrative examples.

EXAMPLE 1

A bovine immunoglobulin fraction was obtained from bovine blood by a process according to the invention, and tested for antibody activity against *E. coli* antigens.

Bovine blood from several animals was collected from an abattoir. Clear plasma was obtained by sedimenting the blood cells by means of a centrifugre.

To 3 liters of the plasma so obtained was added 936 gms of solid ammonium sulfate, to give 0.5 saturation of the plasma with the ammonium sulfate. Precipitation occurred. The precipitate, containing the immunoglobulins was collected on a filter paper, dissolved in about 2.4 liters of 0.9% saline at 60° C with constant stirring for about 20 minutes. The mixture was cooled, and clarified by filtration through a cheesecloth and by centrifugation. 2.5 liters of a slightly hazy solution were thus obtained. 600 gms of solid ammonium sulfate was added to this solution to give 0.4 saturation, and the resulting precipitate was collected on a filter paper. The precipitate was redissolved in about 700 ml. of saline solution, and the resulting solution was dialyzed for 48 hrs. against 2 changes of 0.9% saline (3-4 liters each) at 5° C.

The dialyzed solution was freeze dried, to give a greyish-white powder.

A total of 10.4 liters of plasma was treated in 4 runs in this manner, and the products combined, to give a total of 310 gms of solid powder of immunoglobulins.

The activity of the immunoglobulin preparation thus obtained was tested against antigen preparations from four E. coli serotypes, namely $O_{101}K$ ($RVC_{118}$); $O_{115}K(PS_{3061})$; $O_{78}K_{80}$; and $O_{26}K_{60}$.

The test method used was that of passive hemagglutination, which is a standard test. Briefly, in this test, a dispersion of sheep red blood cells in buffer, at a standard concentration of 5–10 percent is prepared. The antigen (*E. coli* serotype) is added to this dispersion and incubated under standard conditions. Then the red blood cells are removed and washed, to remove residual antigen. The product is red blood cells "coated" with the antigen. The red blood cell dispersion is brought to a standard 2 percent concentration with buffer.

A series of test tubes of immunoglobulin test solution is then prepared, by serial dilution with buffer. The first tube contains 0.1 ml buffer and 0.1 ml test solution. Half of this mixture is diluted with an equal quantity of buffer, to halve the test solution concentration in the next tube. This process is repeated, to give a series of tubes each having a concentration of test solution one half that of the preceding tube. Control tubes are also run.

To each tube, 0.1 ml of coated sheep red blood cells solution is added. Each tube is then incubated and visually observed to see if agglutination of the blood cells has occurred. Where agglutination occurs, the antibody in the test solution has reacted with antigen attached to the blood cells, indicating the activity against the antigen of complete antibodies in the test solution. The results are expressed as the highest dilution at which agglutination is observed.

To determine the activity of incomplete antibodies in the test solution, rabbit anti-bovine immunoglobulin is used. The red blood cells from the complete antibody test are collected, washed, diluted with buffer and incubated with rabbit anti-bovine immunoglobulin as previously described.

For comparison purposes, the tests were also conducted on the initial combined plasma from which the immunoglobulin had been obtained. The results are given in Table 1.

| | E.Coli Serotype | Anti-gen | Titre Complete | Incomplete |
|---|---|---|---|---|
| | $O_{101}K$ ($RVC_{118}$) | O | 1/16 | 1/16 |
| | | K | 1/8 | 1/4 |
| Plasma | $O_{115}K$ ($PS_{3061}$) | O | 1/8 | 1/8 |
| | | K | 1/16 | 1/8 |
| (74 mg protein per ml). | $O_{78}K_{80}$ | O | 1/8 | 1/4 |
| | | K | 1/16 | 1/16 |
| | $O_{26}K_{60}$ | O | 1/16 | 1/32 |
| | | K | 1/4 | — |
| | $O_{101}K(RVC_{118})$ | O | 1/64 | 1/16 |
| | | K | 1/8 | 1/16 |
| Immunoglobulin | $O_{115}K$ ($PS3061$) | O | 1/32 | 1/16 |
| (62 mg protein per ml). | | K | 1/16 | 1/8 |
| | $O_{78}K_{80}$ | O | 1/8 | 1/8 |
| | | K | 1/32 | 1/16 |
| | $O_{26}K_{60}$ | O | 1/64 | 1/8 |
| | | K | 1/16 | 1/4 |

It is seen that the antibody titres of the immunoglobulins are generally some 2-3 times stronger than the plasma levels.

EXAMPLE 2

In this example, a bovine immunoglobulin fraction was prepared from clear bovine blood serum, and tested for activity against *E. coli* cultures.

5.5 liters of bovine plasma, containing sodium citrate as anticoagulant, was warmed to 26° C, and then with vigorous stirring, 110 ml of a 10% calcium chloride solution was added to give a 0.2% calcium chloride concentration in the plasma. The mixture was stirred vigorously for 2 hours. The "stringy" fibrin precipitate was removed by passing the mixture through a 20 mesh screen and the serum was further clarified by adding 2% Celite 545 and filtering.

The clear, pale red filtrate was brought to 0.5 saturation with ammonium sulfate over 1 hr (1750 g ammonium sulfate). After an additional 1 hr, Celite 545 (110 g, 2%) was added and the mixture was filtered.

The filter cake was suspended in 10% sodium chloride solution (4.5 liters). After stirring for 15 minutes, the slurry was heated to 56° C and held there for 15 minutes. The mixture was cooled to 25°–30° C, and then filtered. The filter cake was washed with water (0.5 liters).

The clear, pale orange filtrate (5.25 liters) was brought to 0.4 saturation with ammonium sulfate over 1 hr (1260 gm ammonium sulfate). After 1 hr stirring, Celite 545 (60 gm, 1%) was added and the mixture was filtered. The filter cake was sucked dry, and added to 0.9% sodium chloride solution (550 ml). The mixture was stirred vigorously for 2 hrs, and filtered. The filter cake was washed with 0.9% sodium chloride (100 ml).

The filtrate was dialyzed against 40 volumes of 0.9% sodium chloride over 60 hours at 5° C. The immunoglobulin solution was then sterile filtered through a 0.45 micron Millipore filter. A total volume of 1400 ml immunoglobulin solution was obtained. By Biuret analysis it was shown to have about 11% protein content. By electrophoretic analysis, the protein was shown to be about 90% globulins.

As compared with the process described in Example 1 the process of this example yielded materials which sterile filtered at a much improved rate.

the product was tested by passive hemagglutination against *E. coli* serotypes, as described in Example 1. The results are given in Table 2.

TABLE 2

|  | E. coli Serotype | Antigen | Titre Complete | Incomplete |
|---|---|---|---|---|
| Plasma | O₁₀₁K (RVC 118) | O | 1/16 | 1/8 |
|  |  | K | 1/16 | 1/8 |
|  | O₁₁₅K (PS3061) | O | 1/16 | 1/8 |
|  |  | K | 1/16 | 1/8 |
| Immuno- | O₁₀₁K (RVC 118) | O | 1/64 | 1/32 |
| globulin |  | K | 1/32 | 1/16 |
|  | O₁₁₅K (PS3061) | O | 1/32 | 1/16 |
|  |  | K | 1/32 | 1/16 |

EXAMPLE 3

Immunoglobulin solution prepared according to the present invention was injected into clves, to determine its effect on the incidence of severe scours.

187 calves between 5 and 10 days of age were each given an injection of 60 mls. immunoglobulin solution (10 percent concentration). A control group of 129 calves of similar age was kept under comparable condition, but not injected. 8 days after injection, it was found that only 2.7 percent of the injected calves suffered from severe scours, compared with 23 percent of the control, non-injected group. After 26 days, the mortality due to all causes in the injected group was 10.7 percent, whereas in the control group, the mortality was 17.8 percent.

We claim:

1. A process for preparing a bovine immunoglobulin fraction active against coliform bacteria infection in young calves, which comprises the steps of precipitating out by salt fractionation crude immunoglobulins from bovine plasma or clear bovine serum employing a salt concentration of up to about 0.7 saturation, and removing the crude immunoglobulins so formed; forming an aqueous solution of the crude immunoglobulins in an aqueous solution of up to about 20% (w/v) salt concentration, heating the solution to a temperature of from about 50° C to about 60° C and cooling the solution and then removing coagulated proteins; precipitating out the immunoglobulins by salt fractionation employing a salt concentration of about 0.2 to about 0.6 saturation; separating and redissolving the precipitate in aqueous solution, and purifying the solution by subjection to a molecular sieve procedure.

2. The process of claim 1 wherein the solution which is heated is a solution of crude immunoglobulins in aqueous sodium chloride solution, of up to 20% (w/v) sodium chloride concentration.

3. The process of claim 2 wherein the sodium chloride concentration is about 10% w/v.

4. The process of claim 1 wherein the purification is effected by dialysis against dilute saline.

5. The process of claim 1 which is carried out on clear bovine serum.

6. The process of claim 1 which is carried out on bovine plasma.

7. The process off claim 3 wherein the heating takes place at about 56° C for about 15 minutes.

8. The process of claim 1 including the additional step of adding a preservative to the purified solution.

9. The process of claim 8 wherein the preservative is selected from the group consisting of thimerosal and phenol.

10. The pro cess of claim 1 which includes the step of freeze drying the immunoglobulins after purification.

11. A process as claimed in claim 1 wherein the heating takes place at about 56° C for a short length of time sufficient to inactivate viruses which are present.

12. The process as claimed in claim 1 wherein, after purifying the solution by subjection to a molecular sieve procedure, the solution is sterile filtered and the filtrate containing bovine immunoglobulin is recovered.

13. A process for preparing a bovine immunoglobulin fraction active against coliform bacteria infection in young calves, which comprises the steps of
   a. subjecting bovine plasma or clear bovine serum to salt fractionation with ammonium sulfate of up to about 0.7 saturation, and recovering the crude immunoglobulins that are precipitated;
   b. forming aqueous solution of said crude immunoglobulins in an aqueous sodium chloride solution of up to about 20% (w/v) sodium chloride concentration;
   c. heating said aqueous solution to a temperature of from about 50° C to 60° C; cooling the solution and then removing coagulated proteins;
   d. thereafter subjecting said solution to salt fractionation with ammonium sulfate of about 0.2 to about 0.6 saturation to obtain a precipitate of immunoglobulins;
   e. separating and redissolving the precipitate in aqueous solution; and
   f. purifying the precipitate by subjection to a molecular sieve procedure.

14. A process as claimed in claim 13 wherein said heating step (c) takes place at about 56° C for a short length of time sufficient to inactivate viruses which are present.

15. A process as claimed in claim 14 wherein said heating step takes place for about 15 minutes.

16. The process as claimed in claim 13 wherein, after purifying the solution by subjection to a molecular sieve procedure, the solution is sterile filtered and the filtrate containing bovine immunoglobulin is recovered.

* * * * *